United States Patent [19]
Uflacker

[11] Patent Number: 6,093,203
[45] Date of Patent: Jul. 25, 2000

[54] STENT OR GRAFT SUPPORT STRUCTURE FOR TREATING BIFURCATED VESSELS HAVING DIFFERENT DIAMETER PORTIONS AND METHODS OF USE AND IMPLANTATION

[76] Inventor: Renan Uflacker, 548 Overseer's Retreat, Mount Pleasant, S.C. 29464

[21] Appl. No.: 09/078,340

[22] Filed: May 13, 1998

[51] Int. Cl.[7] ........................................ A61F 2/06
[52] U.S. Cl. .......................... 623/1.12; 623/1.18
[58] Field of Search .................. 623/1, 12, 1.15, 623/1.16, 1.18, 1.19, 1.2, 1.23, 1.35, 1.11, 1.12

[56] References Cited

U.S. PATENT DOCUMENTS

| | | | |
|---|---|---|---|
| 4,503,569 | 3/1985 | Dotter | 606/108 |
| 4,562,596 | 1/1986 | Kornberg | 623/1 |
| 4,733,665 | 3/1988 | Palmaz | 128/343 |
| 4,957,479 | 9/1990 | Roemer | 604/8 |
| 5,211,658 | 5/1993 | Clouse | 623/1 |
| 5,219,355 | 6/1993 | Parodi et al. | 606/191 |
| 5,354,308 | 10/1994 | Simon et al. | 606/198 |
| 5,360,443 | 11/1994 | Barone et al. | 623/1 |
| 5,421,955 | 6/1995 | Lau et al. | 216/48 |
| 5,443,500 | 8/1995 | Sigwart | 623/1 |
| 5,489,295 | 2/1996 | Piplani et al. | 623/1 |
| 5,575,817 | 11/1996 | Martin | 623/1 |
| 5,609,627 | 3/1997 | Goicoechea et al. | 623/1 |
| 5,693,088 | 12/1997 | Lazarus | 623/1 |
| 5,755,775 | 5/1998 | Trerotola et al. | 623/1 |
| 5,772,669 | 6/1998 | Vrba | 606/108 |
| 5,782,906 | 7/1998 | Marshall et al. | 623/1 |
| 5,824,036 | 10/1998 | Lauterjung | 623/1 |
| 5,893,887 | 4/1999 | Jayaraman | 623/1 |
| 5,902,332 | 5/1999 | Schatz | 623/1 |
| 5,938,696 | 7/1999 | Goicoechea et al. | 623/1 |

*Primary Examiner*—David H. Willse
*Assistant Examiner*—Suzette J. Jackson
*Attorney, Agent, or Firm*—Lyon & Lyon LLP

[57] ABSTRACT

A self-expanding stent structure is provided having a main portion that expands to a first diameter and a branch portion that expands to a second diameter, different the first diameter, the main portion having a link portion that forms a flexible linkage to, and forms part of, the branch portion. The self-expanding structure may be compressed to a reduced diameter for delivery, and resumes an expanded diameter during deployment. The self-expanding stent structure also may be advantageously incorporated in an asymmetric stent-graft system. Methods of use are also provided, wherein the main portion of the self-expanding structure, when deployed in a trunk vessel, may be used to anchor the branch portion in a branch vessel.

18 Claims, 5 Drawing Sheets

STENT OR GRAFT SUPPORT STRUCTURE FOR TREATING BIFURCATED VESSELS HAVING DIFFERENT DIAMETER PORTIONS AND METHODS OF USE AND IMPLANTATION

FIELD OF THE INVENTION

The present invention relates generally to minimally invasive techniques for treating occlusive vascular disease, for example, in the carotid, renal, femoral and cerebral arteries, and for repairing aneurysms occurring in bifurcated organs or vessels, such as the abdominal aorta.

BACKGROUND OF THE INVENTION

In recent years a number of minimally invasive techniques have been developed to treat occlusive vascular disease, and to repair aneurysms occurring in organs and vessels.

In occlusive vascular disease, such as arteriosclerosis, plaque accumulates within a vessel and gradually narrows the vessel to the degree that the vessel can no longer supply an adequate flow of blood. A number of vascular prostheses have been developed to re-expand and retain the patency of such afflicted vessels, for example, after atherectomy or angioplasty. U.S. Pat. No. 4,733,665 to Palmaz describes one type of balloon-expandable stent structure to treat occlusive disease.

It is often desirable to support a tortuous vessel, or one having a diameter that changes along the length of the vessel. U.S. Pat. No. 5,421,955 to Lau et al. describes a stent comprising a series of linked sinusoidal rings. That patent describes that the individual sinusoidal elements may be differentially expanded to accommodate diameter changes in the vessel.

A drawback of the foregoing previously known devices, however, is that such devices are not readily deployable in bifurcated vessels, so that one portion of the stent may be deployed in a trunk vessel having a large diameter, and a second portion of the stent may be deployed in a branch vessel having a much smaller diameter. Moreover, because branch vessels often form an angle with trunk vessels, previously known devices cannot be readily employed in such environments.

With respect to treatment of aneurysms, previously known minimally techniques generally seek to "re-line" a flow path through the organ, for example, by fixing a graft across the weakened tissue of the aneurysm. The graft is then held in place with one or more stents, which may be implanted, for example, using a balloon catheter. Such arrangements are described, for example, in Parodi U.S. Pat. No. 5,219,355, European Application No. 0 461 791, and Clouse U.S. Pat. No. 5,211,658.

A number of techniques also have been developed for deploying graft systems in bifurcated anatomy, such as the aorto-iliac bifurcation. For example, U.S. Pat. No. 4,562,596 to Kornberg describes a graft comprising a main portion having first and second legs extending therefrom. The main portion is deployed in the aorta, while the first and second legs are deployed in the iliac arteries. U.S. Pat. No. 5,360,443 to Barone et al. and U.S. Pat. No. 5,489,295 to Piplani et al. describe similar devices.

Other bifurcated graft systems, as described in U.S. Pat. Nos. 5,575,817 to Martin and 5,609,627 to Goicoechea et al., so called "asymmetric grafts," comprise a main portion having a long first leg, and a much shorter second leg. The grafts are deployed so that the long leg is disposed in the iliac artery used to gain access to the aorta, and so that the short leg does not extend into the contralateral iliac artery. In a separate step, an extension portion is then attached to the short leg, thus extending the second leg into the contralateral artery.

In view of the foregoing, it would be desirable to provide a stent having first and second portions that may be deployed to different expanded diameters.

It would further be desirable to provide a stent capable of being deployed in a bifurcated vessel that enables a first portion of the stent to be deployed in a trunk vessel having a first longitudinal axis, and a second portion of the stent to be deployed in a branch vessel having a second longitudinal axis, the second longitudinal axis forming an angle with the first longitudinal axis.

It would be still further desirable to provide a stent structure suitable for use as a support element of a bifurcated graft system.

It would be yet further desirable to provide methods of constructing and deploying a stent-graft system that overcome drawbacks of previously known stent and stent-graft systems.

SUMMARY OF THE INVENTION

In view of the foregoing, it is an object of the present invention to provide a stent having first and second portions that deploy to different expanded diameters.

It is another object of this invention to provide a stent capable of being deployed in a bifurcated vessel, wherein a first portion of the stent is deployed in a trunk vessel having a first longitudinal axis, and a second portion of the stent is deployed in a branch vessel having a second longitudinal axis, the second longitudinal axis forming an angle with the first longitudinal axis.

It is a further object of the present invention to provide a stent structure suitable for use as a support element of a bifurcated graft system.

It is a still further object of the present invention to provide methods of constructing and deploying a stent-graft system that overcome drawbacks of previously known stent and stent-graft systems.

These and other objects of the invention are accomplished by providing a self-expanding stent structure comprising a first portion having a first expanded diameter and a second portion having a second expanded diameter. The self-expanding stent structure comprises a main portion configured to be disposed in a trunk vessel having a first diameter and a branch portion configured to be disposed in a branch vessel having a second diameter different than the first diameter. A continuous flexible link extends from the main portion and forms part of the second portion. The self-expanding structure may be compressed to, and constrained at, a reduced diameter for delivery, and resumes an expanded shape during deployment.

In accordance with the principles of the present invention, the stent structure also may be used to support a graft to treat aneurysms occurring in bifurcated organs or vessels, such as the abdominal aorta. Methods of deploying a stent and stent-graft system constructed in accordance with the present invention are also provided.

BRIEF DESCRIPTION OF THE DRAWINGS

Further features of the invention, its nature and various advantages will be more apparent from the accompanying drawings and the following detailed description of the preferred embodiments, wherein.

DETAILED DESCRIPTION OF THE INVENTION

Figure 1A:
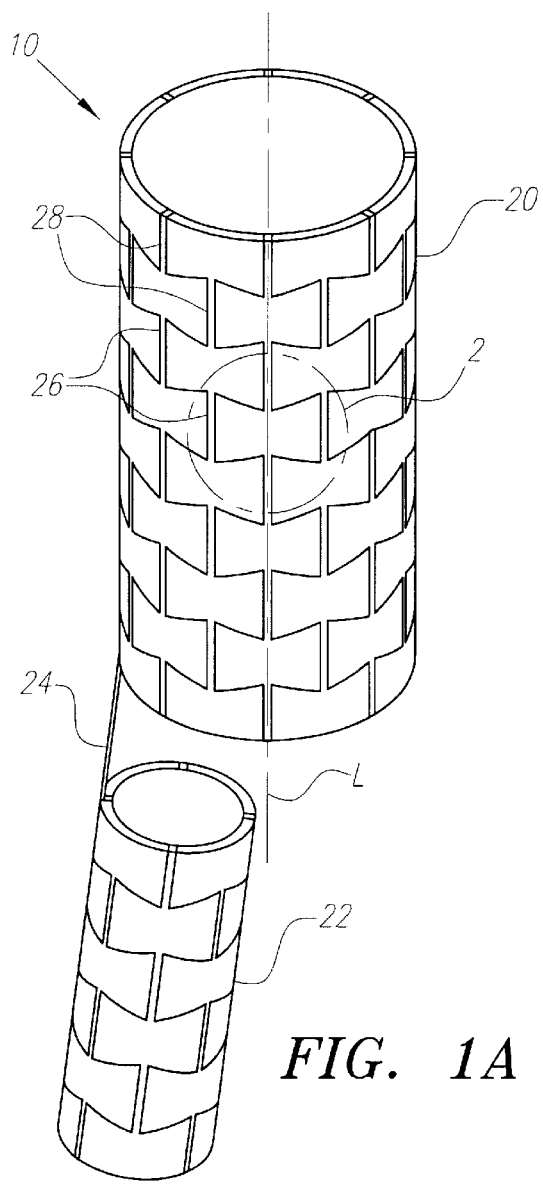
FIGS. 1A and 1B are, respectively, perspective front and side views of a self-expanding stent constructed in accordance with the principles of the present invention in the deployed state.
Figure 1B:
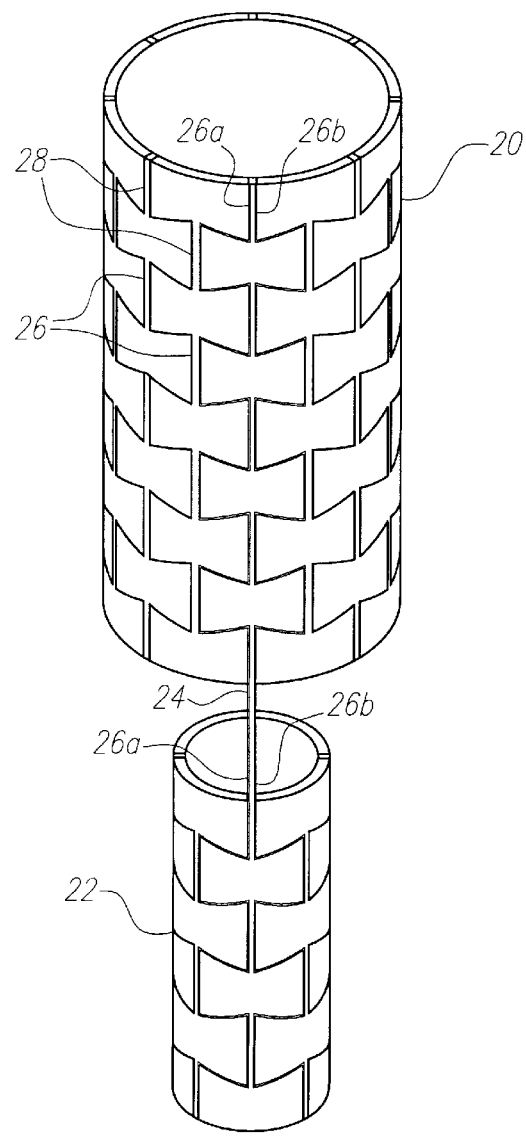

Referring to FIGS. 1A and 1B, stent 10 constructed in accordance with the principles of the present invention is described. Stent 10 comprises self-expanding structure having main portion 20 coupled to branch portion 22 via flexible link 24. Each of main portion 20 and branch portion 22 are formed from a plurality of longitudinal wire segments 26 welded together at points of contact 28. Wire segments 26 preferably comprise a resilient material, such as a nickel-titanium alloy or stainless steel, and permit self-expanding structure 10 to be compressed to a reduced diameter, as described hereinafter.

Flexible link 24 preferably comprises an extension of wire segments 26a and 26b, and forms a part of main portion 20 and branch portion 22. Flexible link 24 permits branch portion 22 to bend out of alignment with longitudinal axis L of main portion 20, so that branch portion 22 is capable of bending to accommodate an angle at which a branch vessel connects to a trunk vessel.

Figure 2A:
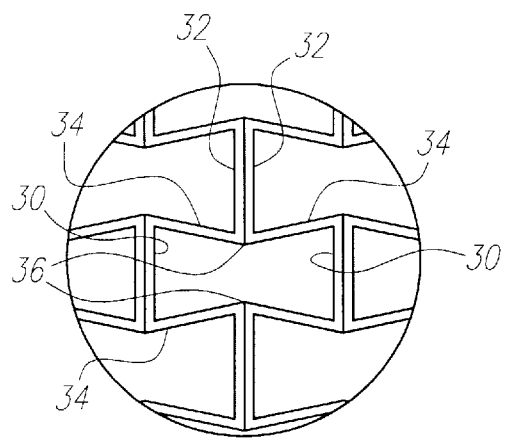
FIGS. 2A and 2B are, respectively, enlarged partial views, within view area 2 of FIG. 1A, of the self-expanding stent structure of FIGS. 1A and 1B in the deployed and delivery states.
Figure 2B:
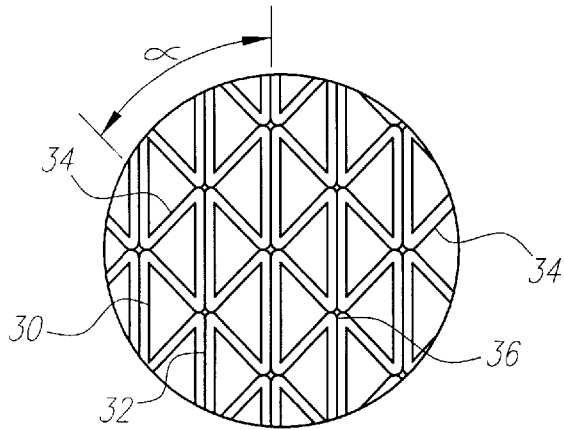

With respect to FIGS. 2A and 2B, each wire segment 26 comprises spaced-apart longitudinal segments 30 and 32 interconnected by connecting elements 34. As shown in FIG. 2A, connecting elements 34 are non-orthogonal to longitudinal segments 30 and 32 when self-expanding stent structure 10 assumes its fully expanded, deployed state (as in FIGS. 1A and 1B). When a radially compressive load is applied to self-expanding structure 10, however, the angle a formed between the connecting elements 34 and longitudinal segments 30 and 32 becomes more acute, thus reducing the circumferential distance between longitudinal segments 30 and 32, as depicted in FIG. 2B. Contraction of self-expanding stent structure 10 also causes apices 36 formed by the wire segments to move towards one another and foreshortens the length of stent 10.

Figure 3A:
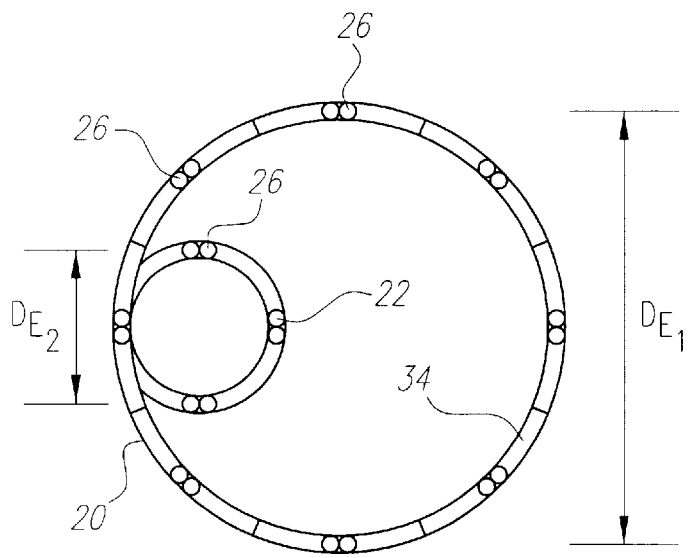
FIGS. 3A and 3B are, respectively, end views of the self-expanding stent structure of FIGS. 1A and 1B in the deployed and delivery states.
Figure 3B:
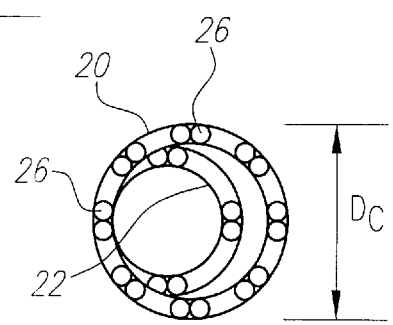

In accordance with the principles of the present invention, stent 10 may be compressed to reduced delivery diameter $D_c$, depicted in FIG. 3B, wherein the diameters of main portion 20 and branch portion 22 are approximately equal. Stent 10 is then constrained at that reduced diameter for transluminal delivery using a delivery sheath. Once the stent is disposed at a desired position in a vessel, the delivery sheath is retracted, releasing the constraint.

Upon release of the constraint imposed by the delivery sheath, the main and branch portions of self-expanding stent 10 resume expanded, deployed diameters $D_{E1}$ and $D_{E2}$, as depicted in FIG. 3A. Alternatively, the self-expanding stent structure may comprise a martensitic nickel-titanium alloy that expands to its deployed state by transitioning to the austenite phase upon being exposed to body temperature, as described in U.S. Pat. No. 4,503,569 to Dotter.

Figure 4A:
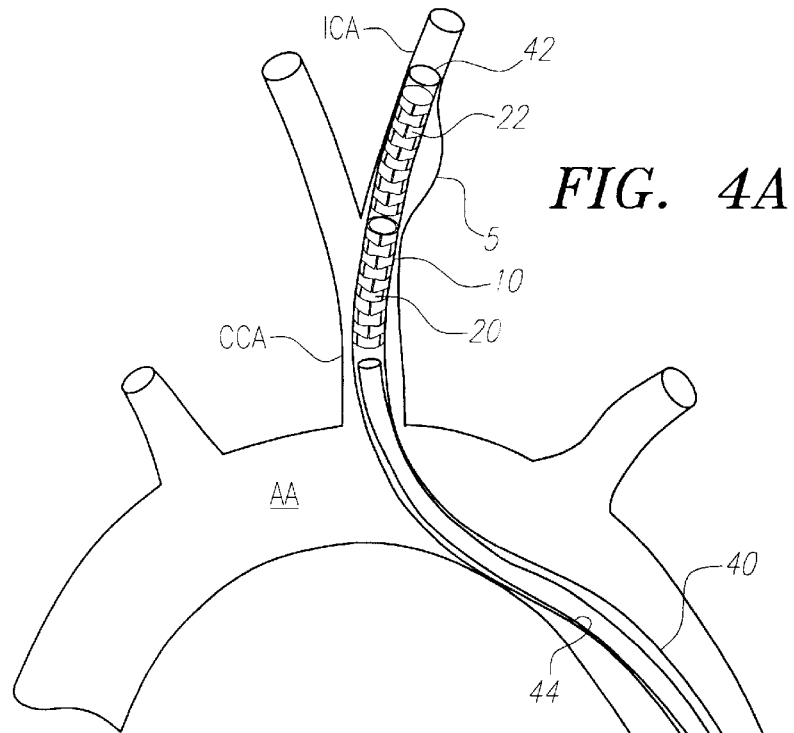
FIGS. 4A and 4B are views depicting deployment of stents constructed in accordance with the present invention at the junctions of the carotid artery and aorta and subclavian artery and aorta.
Figure 4B:
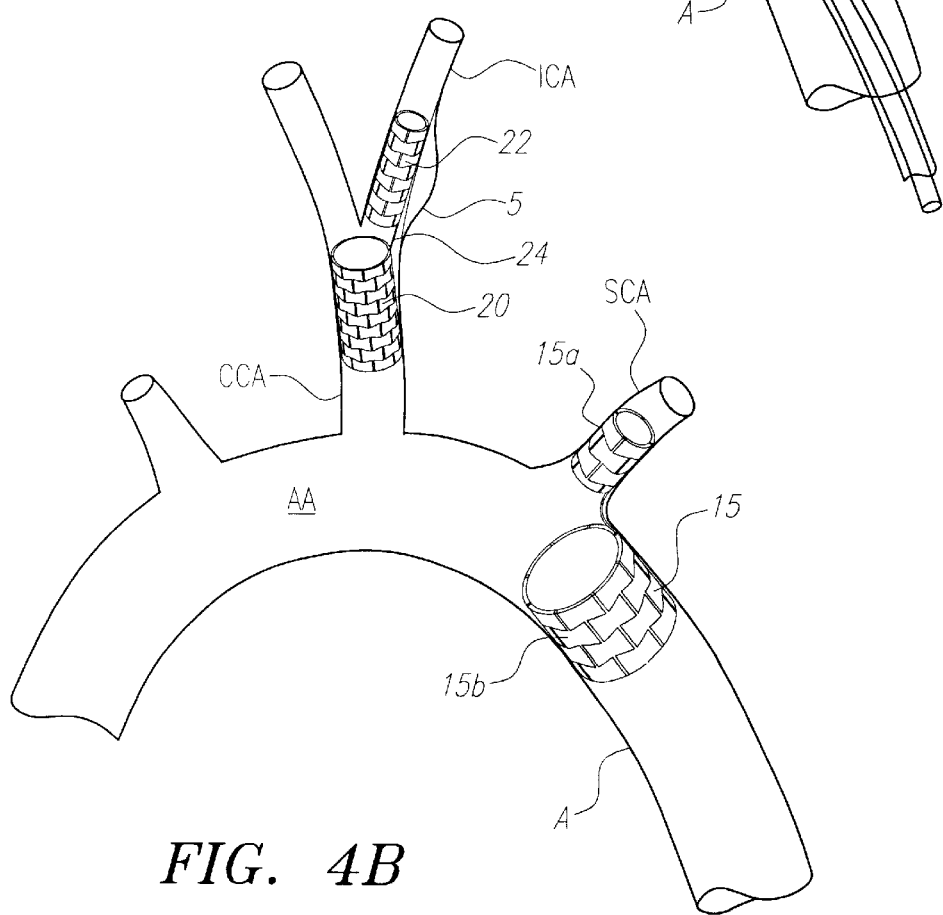

Referring to FIGS. 4A and 4B, a method of using stent 10 to treat stenosis S in a patient's internal carotid artery ICA is described. In FIG. 4A, stent 10 is shown disposed within delivery sheath 40 at its reduced delivery diameter $D_C$. Stent 10 is loaded in delivery sheath 40 so that branch portion 22 is located nearer to distal end 42 of the delivery sheath.

Delivery sheath 40 has distal end 42 positioned within internal carotid artery ICA so that branch portion 22 is aligned with stenosis S. This may be accomplished, for example, by passing delivery sheath 40 in a retrograde fashion through a femoral artery, descending aorta A, and into common carotid artery CCA in aorta arch AA under fluoroscopic guidance. Push tube 44 is disposed within delivery sheath 40 so that its distal end abuts against the proximal end of stent 10.

Once sheath 40 is positioned as shown in FIG. 4A, push tube 44 is held stationary while delivery sheath 40 is retracted in the proximal direction. As delivery sheath 40 is retracted proximally, first branch portion 22 expands to its expanded diameter $D_{E1}$, and then main portion 20 expands to its expanded diameter $D_{E2}$. As shown in FIG. 4B, flexible link 24 permits the main portion to be deployed in the common carotid artery CCA, which has a longitudinal axis disposed at an angle to the longitudinal axis of the internal carotid artery ICA. FIG. 4B also depicts second stent 15, constructed in accordance with the present invention, deployed with branch portion 15a disposed in subclavian artery SCA and main portion 15b anchored in the descending aorta A.

As will be apparent from FIGS. 4A and 4B, a stent constructed in accordance with the present invention, such as stents 10 and 15, enable a first portion of the stent to be deployed in a trunk vessel at a first expanded diameter, and a second portion of the stent to be disposed in a branch vessel at a second expanded diameter, and wherein the axes of the first and second portions are not collinear. Consequently, the stent of the present invention may be employed in situations where only a short length of healthy tissue in the branch vessel is available, by using the main portion, deployed in a trunk vessel, to anchor the branch portion in place. The stent of the present invention therefore may be advantageously employed to treat occlusive disease in a number of other branched vessels, such as the femoral arteries and renal arteries.

Figure 5:
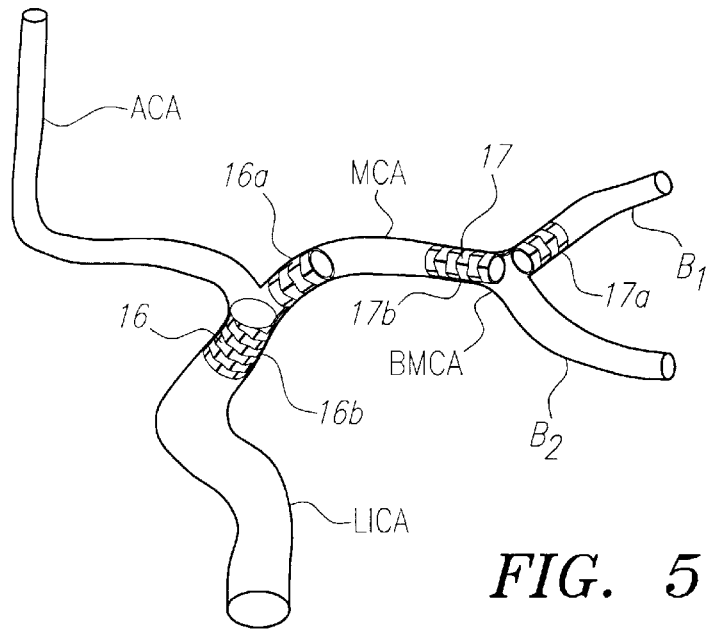
FIG. 5 is a view depicting deployment of stents constructed in accordance with the present invention at the junction of the carotid and cerebral artery and within the cerebral artery.

With respect to FIG. 5, use of stents 16 and 17 of the present invention in the carotid and cerebral arteries is described. Stents 16 and 17 are miniature versions of the stent of FIGS. 1A and 1B. In FIG. 5, stent 16 is disposed with branch portion 16a disposed in middle cerebral artery MCA just distal of the left anterior cerebral artery ACA, while main portion 16b is disposed in left internal carotid artery LICA. Stent 17 is shown disposed with branch portion 17a disposed in a first branch of the middle cerebral artery $B_1$ just distal of bifurcation of the middle cerebral artery BMCA, while main portion 17b is disposed in trunk of the middle cerebral artery MCA.

Figure 6:
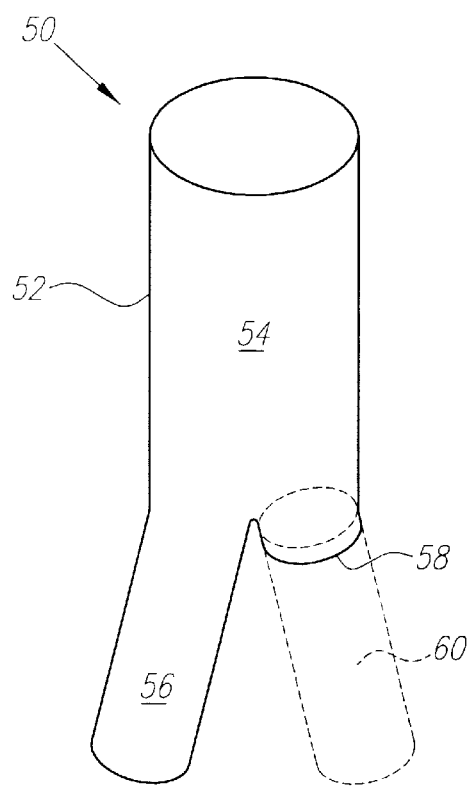
FIG. 6 is a perspective view of an asymmetric stent-graft system incorporating the stent structure of FIG. 1.

Referring now to FIG. 6, stent-graft system 50 constructed in accordance with the present invention is described. Biocompatible graft material 52 is affixed to, and supported by, self-expanding stent structure 10 of FIGS. 1A and 1B (the details of structure 10 are omitted from FIG. 6 for clarity). Graft material 52 may be affixed to either the interior or exterior of structure 10, using, for example, biocompatible sutures. Stent-graft system 50 includes main portion 54 covering main portion 20, branch portion 56 covering branch portion 22, and cuff 58 for accepting covered stent 60.

Covered stent 60 may be constructed, for example, as described in allowed U.S. patent application Ser. No. 08/820,213 to Khosravi et al., which is incorporated herein by reference, and may comprise a coiled sheet stent, such as described in U.S. Pat. No. 5,443,500 to Sigwart, having graft material affixed to its outer surface.

Graft material 52 preferably is a polyester fabric, such as DACRON®, a registered trademark of the E.I. duPont de Nemours Company, Wilmington, or other biocompatible material, such as PTFE (polytetrafluoroethylene). One familiar with the art of graft technology will recognize that other suitable materials also may be used for graft 14.

Figure 7A:
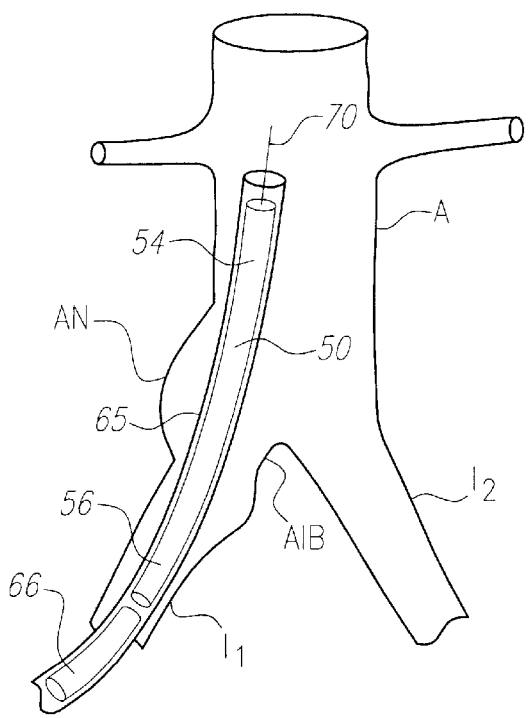
FIGS. 7A–7C are views depicting deployment of the stent-graft system of FIG. 6 in accordance with the methods of the present invention.
Figure 7B:
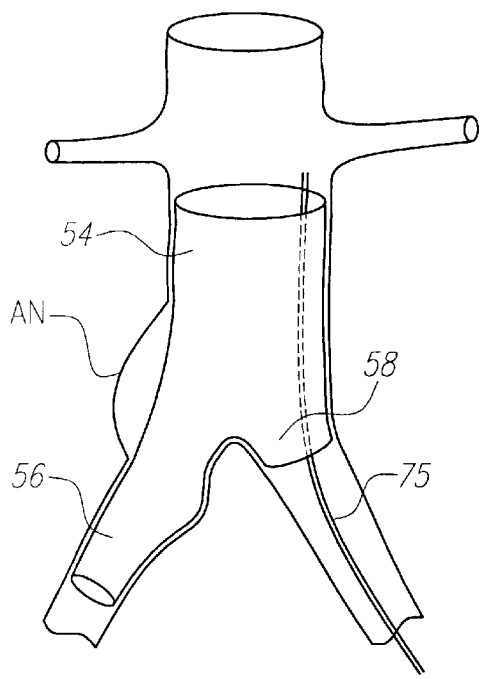
Figure 7C:
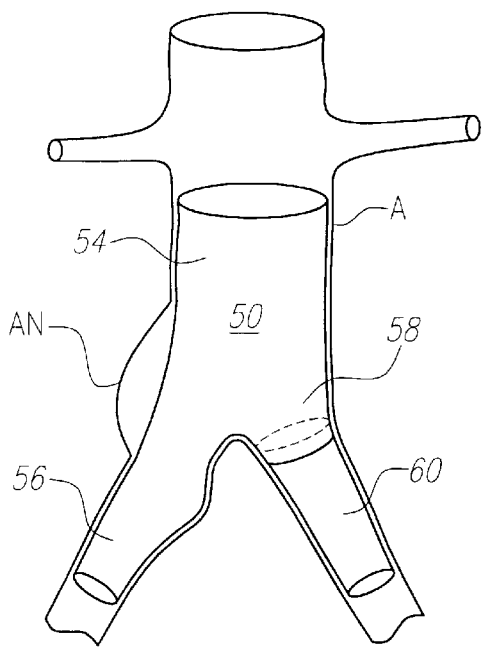

Referring to FIGS. 7A to 7C, deployment of graft 50 in abdominal aorta A to reline aorto-iliac bifurcation AIB having aneurysm AN in accordance with the methods of the present invention is described. In FIG. 7A, graft 50 is shown constrained to its reduced delivery diameter $D_c$ and contained within delivery sheath 65. Delivery sheath 65 is inserted along pre-placed guide wire 70 via a surgical cut-down in a femoral artery. Delivery sheath 65 is then advanced through iliac artery $I_1$ and into abdominal aorta A, so that graft 50 is disposed with main portion 54 in the aorta and branch portion 56 in iliac artery $I_1$. Proper orientation of graft 50 within aorta A may be determined, for example, using radio-opaque bands disposed on the graft or delivery sheath that are visible under a fluoroscope.

Push tube 66 is held stationary and abuts against a proximal end of graft 50 while delivery sheath 65 is withdrawn proximally. As delivery sheath 65 is withdrawn, main portion 20 of self-expanding structure 10 expands to its deployed diameter $D_{E1}$ into contact with the walls of aorta A, so that cuff 58 is aligned with iliac artery $I_2$. As the delivery sheath is further withdrawn, branch portion 22 expands branch portion 56 of graft 50 into contact with iliac artery $I_1$. Delivery sheath 65 is then removed, leaving graft 50 in the state shown in FIG. 7B. Guide wire 75 is then inserted via the contralateral femoral artery, and advanced through iliac artery $I_2$ so that the tip of guide wire 75 passes upward through cuff 58.

A previously known delivery system containing a covered stent, such as described in allowed U.S. patent application Ser. No. 08/820,213 is then advanced along guide wire 75, and covered stent 60 is deployed with one end in cuff 58 and the other end extending into iliac artery $I_2$, completing assembly of the stent graft system. Guide wire 75 is then retracted from the patient.

The foregoing description of the present invention describes treating occlusive disease in the carotid, renal, femoral and cerebral arteries, and for excluding aneurysms occurring in the abdominal aorta. It should be understood, however, the methods and apparatus of the present invention are equally applicable elsewhere in the human body where it is desired to repair a birfucated vessel or organ, or "reline" a hollow-body organ or vessel.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. A method of implanting a structure in an organ or vessel having a trunk and a branch, the method comprising:

providing a self-expanding structure having a main portion coupled to a branch portion by a flexible link;

compressing the self-expanding structure to a reduced delivery diameter and loading the self-expanding structure into a delivery sheath;

inserting the delivery sheath transluminally so that the main portion is disposed in the trunk and the branch portion is disposed in the branch;

retracting the delivery sheath a first distance to enable the main portion to expand to a first deployed diameter, the main portion thereby anchoring the self-expanding structure within the trunk adjacent to the branch; and retracting the delivery sheath a second distance to enable the branch portion to expand to a second deployed diameter, the second diameter different than the first deployed diameter.

2. The method of claim 1 wherein retracting the delivery sheath further comprises exposing the self-expanding structure to a temperature that causes a thermally activated transition.

3. The method of claim 1 wherein the trunk has a first longitudinal axis and the branch has a second longitudinal axis non-collinear with the first longitudinal axis, and after retracting the delivery sheath a first distance, the delivery sheath is rotated to coincide with the second longitudinal axis before retracting the delivery sheath the second distance.

4. A method of implanting a structure in a carotid or cerebral artery having a trunk and a branch, the method comprising:

providing a self-expanding structure having a main portion coupled to a branch portion by a flexible link, the self-expanding structure being constrained at a reduced delivery diameter, the main portion being self-expanding to a first expanded diameter, and the branch portion being self-expanding to a second expanded diameter smaller than the first expanded diameter;

inserting the self-expanding structure in its reduced delivery diameter transluminally so that the main portion is disposed in the trunk and the branch portion is disposed in the branch; and releasing the self-expanding structure such that the main and branch portions self-expand to the first and second expanded diameters, respectively, the self-expanding structure being released while maintaining the main and branch portions in the trunk and branch, respectively.

5. The method of claim 4, wherein the self-expanding structure is constrained at the reduced delivery diameter by a delivery sheath.

6. The method of claim 5, wherein the step of releasing the self-expanding structure comprises retracting the delivery sheath.

7. The method of claim 6, wherein the step of retracting the delivery sheath comprises the steps of retracting the delivery sheath a first distance to enable the branch portion to expand to the second expanded diameter, and retracting the delivery sheath a second distance to enable the main portion to expand to the first expanded diameter, the main portion anchoring the self-expanding structure within the carotid or cerebral artery.

8. The method of claim 5, wherein the step of releasing the self-expanding structure further comprises removing a constraint applied to the self-expanding structure that maintains the self-expanding structure at the reduced delivery diameter.

9. The method of claim 5, wherein the step of releasing the self-expanding structure further comprises exposing the self-expanding structure to a temperature that causes a thermally activated transition.

10. The method of claim 4, wherein the step of releasing the self-expanding structure comprises the step of deploying the main portion in the trunk to anchor the branch portion within the branch.

11. The method of claim 4, wherein the step of inserting the self-expanding structure comprises the step of positioning the main portion in one of a carotid artery, an aorta or a cerebral artery.

12. The method of claim 4, wherein the trunk is selected from the group consisting of a carotid artery and a cerebral artery.

13. The method of claim 4, wherein the branch comprises a stenosis, the releasing step comprising releasing the branch portion to open the stenosis as the branch portion self-expands to the second expanded diameter.

14. The method of claim 4, wherein the self-expanding structure comprises a plurality of longitudinal segments connected by connecting elements non-orthogonal to the longitudinal segments, axially adjacent longitudinal segments moving away from one another as the main and branch portions self-expand to the first and second expanded diameters.

15. A method of implanting a structure in a carotid or cerebral artery having a trunk and a branch extending therefrom, the method comprising:

providing a self-expanding structure having a main portion coupled to a branch portion by a flexible link, the self-expanding structure being constrained at a reduced delivery diameter, the main portion being self-expanding to a first expanded diameter, and the branch portion being self-expanding to a second expanded diameter smaller than the first expanded diameter;

inserting the self-expanding structure in its reduced delivery diameter transluminally so that the main portion is disposed in the trunk of the carotid or cerebral artery and the branch portion is disposed in the branch; and releasing the self-expanding structure such that the main and branch portions self-expand to the first and second expanded diameters, respectively.

16. The method of claim 15, wherein the self-expanding structure comprises a plurality of longitudinal segments connected by connecting elements non-orthogonal to the longitudinal segments, axially adjacent longitudinal segments moving away from one another as the main and branch portions self-expand to the first and second expanded diameters.

17. The method of claim 15, wherein the trunk is a common carotid artery and the branch is an internal carotid artery.

18. The method of claim 15, wherein the branch comprises a stenosis, the releasing step comprising releasing the branch portion to open the stenosis as the branch portion self-expands to the second expanded diameter.

* * * * *